United States Patent
Ohno et al.

(10) Patent No.: US 10,451,545 B2
(45) Date of Patent: Oct. 22, 2019

(54) OPTICAL TEST APPARATUS AND OPTICAL TEST METHOD

(71) Applicant: Kabushiki Kaisha Toshiba, Tokyo (JP)

(72) Inventors: Hiroshi Ohno, Yokohama Kanagawa (JP); Hiroya Kano, Tokyo (JP); Hideaki Okano, Yokohama Kanagawa (JP); Yoshinori Honguh, Yokohama Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 15/899,796

(22) Filed: Feb. 20, 2018

(65) Prior Publication Data

US 2018/0372625 A1    Dec. 27, 2018

(30) Foreign Application Priority Data

Jun. 22, 2017 (JP) .................................. 2017-122606

(51) Int. Cl.
| | |
|---|---|
| *G01N 21/41* | (2006.01) |
| *G01N 23/02* | (2006.01) |
| *G01N 21/17* | (2006.01) |
| *G01N 23/20* | (2018.01) |

(Continued)

(52) U.S. Cl.
CPC ..... *G01N 21/4133* (2013.01); *G01N 21/1702* (2013.01); *G01N 21/4795* (2013.01); *G01N 23/02* (2013.01); *G01N 23/20* (2013.01); *G01N 29/2418* (2013.01); *G01N 21/41* (2013.01); *G01N 21/4788* (2013.01); *G01N 2201/02* (2013.01)

(58) Field of Classification Search
CPC .......... G01N 21/4133; G01N 21/1702; G01N 23/02; G01N 2201/02
See application file for complete search history.

(56) References Cited

U.S. PATENT DOCUMENTS

| | | | |
|---|---|---|---|
| 5,426,505 A * | 6/1995 | Geiser | ..................... G01N 21/45 356/128 |
| 6,349,128 B1 | 2/2002 | Nelson | |

(Continued)

FOREIGN PATENT DOCUMENTS

| | | |
|---|---|---|
| JP | 2003-532114 A | 10/2003 |
| JP | 2008-020329 A | 1/2008 |

(Continued)

*Primary Examiner* — Sang H Nguyen
(74) *Attorney, Agent, or Firm* — Finnegan, Henderson, Farabow, Garrett & Dunner, L.L.P.

(57) ABSTRACT

According to one embodiment, an optical test apparatus includes a photodetector and a processing circuit. The photodetector outputs, as a light receiving signal, information concerning a light direction of received light. The processing circuit processes the light receiving signal to acquire information concerning a standard light direction as a standard and information concerning a passing light direction of passed light which has passed through an object; compares the information concerning the passing light direction with the information concerning the standard light direction, and on the basis of results of the comparison, acquires information concerning internal physical quantities of the object.

12 Claims, 5 Drawing Sheets

(51) Int. Cl.
*G01N 29/24* (2006.01)
*G01N 21/47* (2006.01)

(56) References Cited

U.S. PATENT DOCUMENTS

| | | | |
|---|---|---|---|
| 2002/0005951 A1* | 1/2002 | Fukasawa | G01N 21/3586 |
| | | | 356/432 |
| 2002/0067480 A1* | 6/2002 | Takahashi | G01N 21/3581 |
| | | | 356/317 |
| 2005/0082479 A1* | 4/2005 | Wallace | G01N 21/3586 |
| | | | 250/330 |
| 2008/0013071 A1* | 1/2008 | Tsumura | G01N 21/3581 |
| | | | 356/51 |
| 2008/0123079 A1 | 5/2008 | Numata et al. | |
| 2008/0151239 A1 | 6/2008 | Iketaki | |
| 2016/0113507 A1* | 4/2016 | Reza | G01N 21/1717 |
| | | | 356/477 |
| 2018/0292309 A1* | 10/2018 | Prasad | G01N 21/1702 |

FOREIGN PATENT DOCUMENTS

| | | |
|---|---|---|
| JP | 2008-134186 A | 6/2008 |
| JP | 2008-157873 A | 7/2008 |

\* cited by examiner

OPTICAL TEST APPARATUS AND OPTICAL TEST METHOD

CROSS-REFERENCE TO RELATED APPLICATIONS

This application is based upon and claims the benefit of priority from Japanese Patent Application No. 2017-122606, filed Jun. 22, 2017, the entire contents of which are incorporated herein by reference.

FIELD

Embodiments described herein relate generally to an optical test apparatus and an optical test method in which internal inspection is possible without contact.

BACKGROUND

As a technology to measure a spatial distribution of desired physical quantities of an object, contact type internal measurement and destructive internal measurement have been conventionally employed.

DETAILED DESCRIPTION

Figure 1:
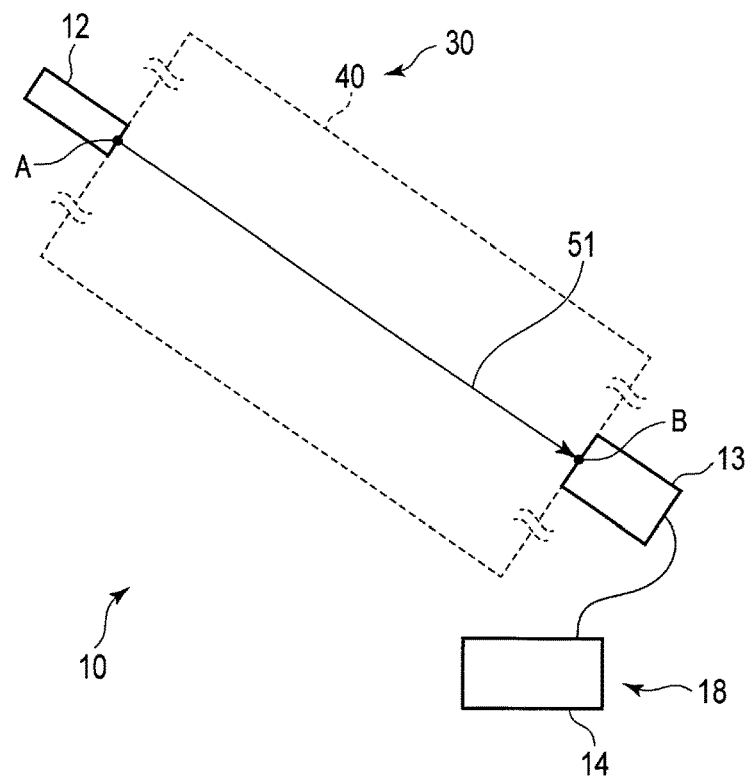
FIG. 1 is a schematic diagram showing a constitutional example of an optical test apparatus according to a first embodiment.

In the contact type internal measurement and the destructive internal measurement, it is worried that the physical quantities of the object change during the contact and the destruction, and hence, the measurement of the correct quantities has been demanded.

According to one embodiment, an optical test apparatus includes a photodetector and a processing circuit. The photodetector outputs, as a light receiving signal, information concerning a light direction of received light. The processing circuit processes the light receiving signal to acquire information concerning a standard light direction as a standard and information concerning a passing light direction of passed light which has passed through an object; compares the information concerning the passing light direction with the information concerning the standard light direction, and on the basis of results of the comparison, acquires information concerning internal physical quantities of the object.

According to one embodiment, an optical test apparatus includes a photodetector and a processing circuit. The photodetector outputs, as a light receiving signal, information concerning a light position of received light. The processing circuit processes the light receiving signal to acquire information concerning a standard light position as a standard and information concerning a passing light position of passed light which has passed through an object, compares the information concerning the passing light position with the information concerning the standard light position, and on the basis of results of the comparison, acquires information concerning internal physical quantities of the object.

According to one embodiment an optical test method receives passed light which has passed through an object, acquires information concerning a standard light direction or a standard light position that is a standard as standard light information, acquires information concerning a passing light direction or a passing light position of the received passed light as passing light information, compares the passing light information with the standard light information, and on the basis of results of the comparison, acquires information concerning internal physical quantities of the object.

Various Embodiments will be described hereinafter with reference to the accompanying drawings. It is to be noted that the drawings are schematic or conceptual, and do not necessarily reflect an actual relation between a thickness and a width in each component, an actual ratio of a size between the components, or the like. Furthermore, even the same part might be shown in a different dimension or at a different ratio depending on the drawings. In the present description and the respective drawings, elements similar to those already described with reference to the drawings are denoted with the same reference signs and detailed descriptions are suitably omitted.

First Embodiment

Hereinafter, description will be made as to an optical test apparatus and an optical test method according to the present embodiment in detail with reference to the drawings.

Initially, description is made as to a constitution of the optical test apparatus according to the present embodiment. FIG. 1 is a schematic diagram showing a constitutional example of an optical test apparatus 10 according to the present embodiment. In addition to the schematic constitutional example of the optical test apparatus 10, FIG. 1 schematically shows one example of a light path of probe beam 51 (detection light) and a test region 30.

It is to be noted that hereinafter, description will be made as to an example where a measurement object (an object 40)

by the optical test apparatus 10 according to the present embodiment is a gas, but the present embodiment is not limited to this example. The object 40 may be a liquid or a solid which is present in the test region 30. However, when the object 40 is the gas, the gas which is present in the test region 30, e.g., a substance filled in the test region 30 can be treated as the object 40.

As shown in FIG. 1, the optical test apparatus 10 according to the present embodiment comprises a probe beam generating unit 12, a photodetector 13, and a processing circuit 14.

The probe beam generating unit 12 according to the present embodiment emits the probe beam 51 toward the object 40. The probe beam generating unit 12 includes, for example, a light source and a condensing optical system. The condensing optical system includes, for example, a collimator. At this time, the light (an electromagnetic wave) emitted from the light source is focused as parallel light by the condensing optical system, to irradiate the object 40 as the probe beam 51.

It is to be noted that the probe beam generating unit 12 according to the present embodiment may be configured to acquire an emission angle of the probe beam 51 to be emitted. Here, the emission angle is, for example, an angle formed by an optical axis of the probe beam generating unit 12 and the probe beam 51 emitted by the probe beam generating unit 12. In other words, the emission angle corresponds to a light direction when the light (the probe beam 51) is emitted. Hereinafter, the light direction of the probe beam 51 to be emitted by the probe beam generating unit 12 will be referred to as a first light direction.

It is to be noted that a wavelength of the probe beam 51 according to the present embodiment may be any wavelength transmittable or passable through the object 40, for example, the substance filled in the test region 30 when the measurement object is the gas, as long as the wavelength is selected in accordance with the object 40. The probe beam 51 may be, for example, an X-ray, visible light or a microwave.

Furthermore, the probe beam generating unit 12 according to the present embodiment may be configured to emit light (the electromagnetic wave) including wavelengths, as the probe beam 51. Additionally, the probe beam 51 may be the light including a single wavelength or the wavelengths.

Additionally, the probe beam generating unit 12 according to the present embodiment does not have to comprise the light source. In this case, in the optical test apparatus 10, there is usable light (an electromagnetic wave) to be emitted from an external light source for the optical test apparatus 10 in place of the light source, or natural light such as sunlight. Furthermore, in this case, for example, an optical element which selectively transmits or reflects light of a specific wavelength region is used as the probe beam generating unit 12. Specifically, the probe beam generating unit 12 of the present embodiment may be any unit (section) as long as the unit can emit, to the object 40, the probe beam 51 having characteristics in accordance with the object.

It is to be noted that in the present embodiment, the electromagnetic wave is occasionally referred to as the light, but when the light is referred, it is not intended that the visible light is only indicated. Hereinafter, in the present embodiment, there will be described an example where the probe beam generating unit 12 is configured to emit the electromagnetic wave including or considered to include the single wavelength, as the probe beam 51.

The photodetector 13 according to the present embodiment receives the probe beam 51 emitted by the probe beam generating unit 12. For example, the probe beam 51 to be received by the photodetector 13 includes the probe beam 51 transmitted or passed through the object 40. Furthermore, the photodetector 13 is configured to measure or detect an incident angle of the probe beam 51 to be received into the photodetector 13. Here, the incident angle into the photodetector 13 is an angle formed by an optical axis of the photodetector 13 and the light to be received by the photodetector 13. In other words, the incident angle corresponds to the light direction when the light (the probe beam 51) enters the photodetector 13. Hereinafter, the light direction of the probe beam 51 to enter the photodetector 13 will be referred to as a second light direction. The photodetector 13 outputs information concerning the measured or detected second light direction as a light receiving signal to the processing circuit 14.

The photodetector 13 comprises, for example, at least two light receiving surfaces. Alternatively, the photodetector 13 may be constituted of a combination of one light receiving surface and a pinhole, or a combination of one light receiving surface and lenses. Here, description is made as to the example where the photodetector comprises two light receiving surfaces. The respective light receiving surfaces are disposed vertically to an optical axis direction of the photodetector 13. That is, the respective light receiving surfaces are disposed in parallel with each other. A distance between the light receiving surfaces in the optical axis direction of the photodetector 13 is beforehand recorded in the photodetector 13 or the processing circuit 14, and hence, the distance is information known in this manner. Furthermore, for the respective light receiving surfaces, it is possible to detect and output a position in each light receiving surface at which the light is received. Here, for the sake of simplicity, description is made as to an example where the photodetector 13 comprises two light receiving surfaces of a first light receiving surface and a second light receiving surface disposed to face the object 40 away from the first light receiving surface. At this time, a distance between the first light receiving surface and the second light receiving surface is known. Furthermore, the probe beam 51 transmitted or passed through the first light receiving surface has strength with which the light is detected by at least the second light receiving surface. Additionally, when the probe beam 51 is transmitted or passed through the first light receiving surface, the light direction of the probe beam 51 does not change, or when the probe beam 51 is transmitted or passed through the first light receiving surface, a change quantity of the light direction of the probe beam 51 is known. The photodetector 13 having such a constitution outputs at least information concerning a first light receiving position in the first light receiving surface and a second light receiving position in the second light receiving surface, as the information concerning the second light direction to the processing circuit 14.

It is to be noted that in the present embodiment, description is made as to the example where inclination of the optical axis of the photodetector 13 does not change, but the present embodiment is not limited to this example. For example, the inclination of the optical axis of the photodetector 13 may change. In this case, the inclination of the optical axis is detected by the photodetector 13 or acquired from the outside.

Furthermore, a relative position and a relative angle between the optical axis of the probe beam generating unit 12 and the optical axis of the photodetector 13 may be fixed.

For example, when the relative angle is not fixed, an angle on the side of the unit having a degree of freedom of the angle may be detected.

The processing circuit 14 according to the present embodiment processes the light receiving signal to be output by the photodetector 13. The processing includes, for example, processing to calculate the incident angle (the second light direction) of the probe beam 51 into the photodetector 13. For example, the second light direction is calculated as an angle formed by a vector from the first light receiving position toward the second light receiving position and a vector from an optical axis position in the first light receiving surface toward an optical axis position in the second light receiving surface. The processing circuit 14 of the present embodiment acquires information concerning a standard light direction as a standard, for example, from the probe beam generating unit 12, the photodetector 13 or the like. The processing circuit 14 performs processing to compare the acquired information concerning the second light direction with the information concerning the standard light direction as the standard. Furthermore, the processing circuit 14 of the present embodiment performs processing to compare pieces of the information concerning the second light direction calculated from pieces of information acquired at different timings. That is, the processing circuit 14 performs processing to acquire a time-series change of the second light direction (the light receiving signal). Furthermore, the processing circuit 14 of the present embodiment calculates or acquires information concerning internal physical quantities of the object 40 on the basis of results of the comparison of the information concerning the light direction. The processing circuit 14 may comprise a function of a judging unit which performs various judgments concerning the calculation or acquisition of the information.

It is to be noted that, for example, the photodetector 13 may perform the calculation of the second light direction and the acquisition of the time-series change of the second light direction. In this case, the photodetector 13 calculates the incident angle (the second light direction) of the probe beam 51 into the photodetector 13 as described above. Furthermore, the photodetector 13 outputs, to the processing circuit 14, the calculated incident angle (the second light direction) as the information concerning the light direction of the light (the probe beam 51) transmitted or passed through the object 40.

The optical test apparatus 10 according to the present embodiment further comprises a control circuit 18. The control circuit 18 is constituted to control an operation of each unit (section) of the optical test apparatus 10. The control circuit 18 may comprise the processing circuit 14. It is to be noted that the control circuit 18 or a part of the control circuit 18 may be disposed in at least one of the probe beam generating unit 12 and the photodetector 13. Each of the processing circuit 14 and the control circuit 18 may be an integrated circuit, for example, such as a Central Processing Unit (CPU), an application Specific Integrated Circuit (ASIC), or the like. Furthermore, although not shown in the drawings, the optical test apparatus 10 of the present embodiment further comprises a power source unit and a recording circuit. The power source unit is constituted to supply power to each unit of the optical test apparatus 10. The recording circuit is configured to record, for example, the time-series change of the second light direction (the incident angle of the probe beam 51 into the photodetector 13) which is calculated and output by the processing circuit 14. Additionally, in the recording circuit, there are recorded processing programs and various parameters for use in the optical test apparatus 10. Any processing concerning an operation of the optical test apparatus 10 is executed in accordance with each program recorded, for example, in the recording circuit. The respective programs may be beforehand recorded in the optical test apparatus 10 or may be read from an external recording medium for the optical test apparatus 10. Furthermore, the recording circuit temporarily records an output value of the photodetector 13 and data which is being processed in the processing circuit 14. The recording circuit may be a volatile memory or a nonvolatile memory. It is to be noted that a part of the recording circuit may be disposed in the photodetector 13 or the processing circuit 14.

The photodetector 13 is connected to the processing circuit 14, for example, so that the data is transferable. It is to be noted that the connection of the photodetector 13 to the processing circuit 14 may be wired or wireless. For example, when the photodetector 13 comprises the recording circuit, the photodetector 13 does not have to be connected to the processing circuit 14 during measurement of the incident angle of the probe beam 51 into the photodetector 13 by the photodetector 13. In this case, the data transfer may be performed via the external recording medium, e.g., a flash memory or the like.

It is to be noted that the test region 30 according to the present embodiment is disposed, for example, on the light path of the probe beam 51 which can be entered the photodetector 13 after emitted by the probe beam generating unit 12 and between an emission end of the probe beam generating unit 12 from which the probe beam 51 is to be emitted and an entrance end of the photodetector 13 which receives the probe beam 51. Therefore, a range of a size of the test region 30 is adjusted so that the test region 30 can be disposed on the light path of the probe beam 51, and depends on a distance between the emission end and the entrance end, the emission angle at which the probe beam generating unit 12 can emit the probe beam 51, and a light receiving angle at which the photodetector 13 can receive the probe beam 51.

Figure 2:
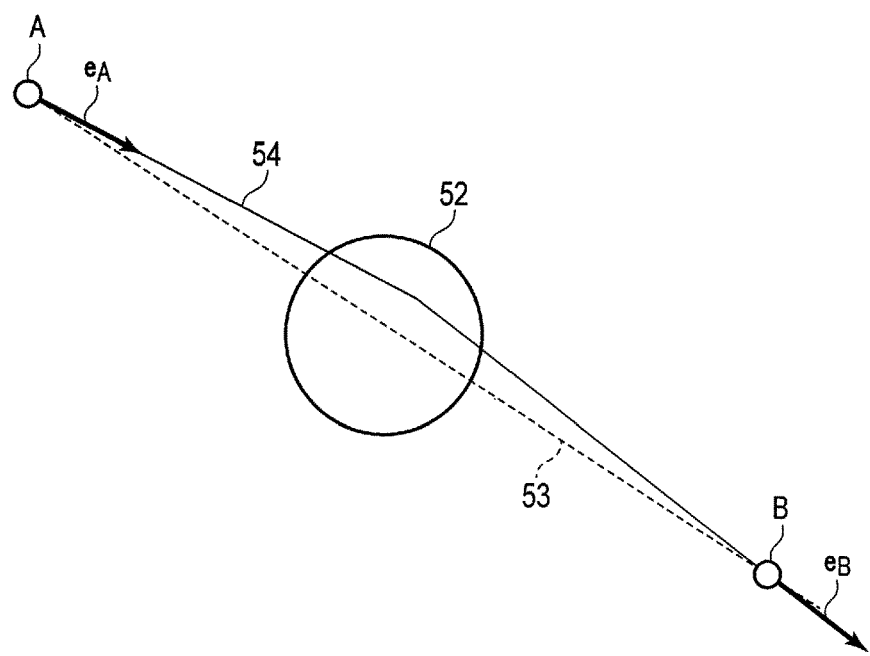
FIG. 2 is a schematic diagram to explain a measurement principle of the optical test apparatus according to the first embodiment.

The optical test apparatus 10 according to the present embodiment acquires the information concerning the internal physical quantities of the object 40 without contact to the object 40. Here, in the optical test apparatus 10 of the present embodiment, description is made as to a principle to acquire information concerning a refractive index distribution in the object 40 as the information concerning the internal physical quantities of the object 40 with reference to a schematic diagram shown in FIG. 2. In FIG. 2, for example, the light (the electromagnetic wave) is emitted from a position A. At this time, the light emitted from the position A to reach a position B is considered.

It is to be noted that the light (the probe beam 51) to be emitted from the position A may have a wavelength transmittable or passable through the substance (the object 40) present between the position A and the position B. That is, the light to be emitted from the position A may be selected in accordance with the substance, and may be, for example, the X-ray, the visible light or the microwave.

Here, when a distance along the light path is s, a positional vector on the light path is r=r(s) and a refractive index at a point indicated by the positional vector r=r(s) is n(r), an equation of the light which indicates the light path is obtained as follows:

$$\frac{d}{ds}\left(n(\vec{r})\frac{d\vec{r}}{ds}\right) = \nabla n(\vec{r}).$$

Equation (1)

Furthermore, when Equation (1) is integrated along the light path from the position A to the position B, Equation (1) is developed as follows:

$$\frac{d\vec{r}_B}{ds} = \frac{1}{n(\vec{r}_B)} \int_A^B ds \nabla n(\vec{r}) + \frac{n(\vec{r}_A)}{n(\vec{r}_B)} \frac{d\vec{r}_A}{ds}, \quad \text{Equation (2)}$$

in which rA is a positional vector indicating the position A, rB is a positional vector indicating the position B, n(rA) is a refractive index at the position A, and n(rB) is a refractive index at the position B.

Here, when a unit vector indicating the light direction at the point indicated by the positional vector r=r(s) is e=e(r), the unit vector e is represented as follows.

$$\vec{e} = \frac{d\vec{r}}{ds}. \quad \text{Equation (3)}$$

When Equation (3) is used, Equation (2) is developed as follows.

$$\vec{e}_B = \frac{1}{n(\vec{r}_B)} \int_A^B ds \nabla n(\vec{r}) + \frac{n(\vec{r}_A)}{n(\vec{r}_B)} \vec{e}_A. \quad \text{Equation (4)}$$

Here, a vector eA is a unit vector indicating the light direction at the position A, and a vector eB is a unit vector indicating the light direction at the position B.

Here, for example, it is considered that a refractive index distribution 52 is not present on the light path of the light which can be reached the position B after emitted from the position A. When the refractive index distribution 52 is not present on the light path, the refractive index n(r) is constant in the light path. At this time, n(rA)=n(rB), and hence, Equation (4) is developed as follows.

$$\vec{e}_A = \vec{e}_B \quad \text{Equation (5)}.$$

Therefore, when the refractive index distribution 52 is not present on the light path, the unit vector e indicating the light direction is constant irrespective of its position on the light path. In this case, the path of the light which can be reached the position B after emitted from the position A is a straight line which passes the position A and the position B as shown by a broken line 53 in FIG. 2.

On the other hand, when the refractive index distribution 52 is present on the light path, n(rA)=n(rB) is not established and hence, the vector eB is different from the vector eA. That is, when the refractive index distribution 52 is present on the light path, the light direction at the position B is different from the light direction at the position A of the light which can be reached the position B after emitted from the position A. In this case, a path of the light which can be reached the position B after emitted from the position A is, for example, a path different from the path shown by the broken line 53, as shown by a solid line 54 in FIG. 2. In other words, when the vector eB is different from the vector eA, the refractive index distribution 52 is present on the light path.

In this way, it is possible to confirm whether or not the refractive index distribution 52 is present on the light path, from the comparison of the vector eA with the vector eB. Furthermore, when the vector eA is constant, a change of the vector eB indicates a change of the refractive index distribution 52 on the light path. However, even in this case, when the vector eB can be acquired in a state (a standard state) where the refractive index distribution 52 is not present on the light path, the change of the vector eB between the standard state and a state at arbitrary time indicates the presence of the refractive index distribution 52.

Here, description is made as to an operation of the optical test apparatus 10 according to the present embodiment. In the present embodiment, an example where the object 40 is a gas will be described. Therefore, in the optical test apparatus 10 of the present embodiment, for example, as shown in FIG. 1, the emission end of the probe beam generating unit 12 corresponds to the above-mentioned position A and the entrance end of the photodetector 13 corresponds to the above-mentioned position B. Specifically, the optical test apparatus 10 acquires the information concerning the refractive index distribution on the light path of the probe beam 51 between the probe beam generating unit 12 and the photodetector 13, as information concerning the internal physical quantities of the object.

It is to be noted that when the object 40 is a liquid or a solid, a light path in the object 40 may be considered among light paths in the test region 30. In this case, the light direction of the probe beam 51 can change, when the probe beam 51 enters the object 40 in the test region 30 and when the probe beam 51 exits from the object 40 in the test region 30. Therefore, in the light path in the object 40, an end (a surface) on the side of the probe beam generating unit 12 is defined as the position A and the other end (on the side of the photodetector 13, i.e., a back surface) is defined as the position B.

Initially, for example, there is considered an example where the optical test apparatus 10 of the present embodiment can acquire the first light direction (the vector eA). In this case, the processing circuit 14 acquires the first light direction as the standard light direction. The photodetector 13 measures the second light direction (the vector eB) of the received probe beam 51 which has passed through the object 40. The photodetector 13 outputs the information concerning the measured second light direction to the processing circuit 14. The processing circuit 14 acquires the second light direction as a passing light direction of the passed light (the probe beam 51) which has passed through the object 40. The processing circuit 14 compares the passing light direction with the acquired standard light direction. On the basis of results of the comparison, the processing circuit 14 acquires information concerning the presence/absence of the refractive index distribution 52 on the light path of the probe beam 51, as the information concerning the internal physical quantities of the object 40. Here, when the standard light direction is the same as the passing light direction, it is judged that the refractive index distribution 52 is not present on the light path of the probe beam 51 (the passed light). On the other hand, when the passing light direction is different from the standard light direction, it is judged that the refractive index distribution 52 is present on the light path of the probe beam 51 (the passed light). Such judgment is performed, for example, by the processing circuit 14, but the present embodiment is not limited to this example. Various judgments of the acquisition of the information concerning the internal physical quantities of the object 40 can be performed by an external processing circuit for the optical test apparatus 10 or a user. In this case, the processing circuit 14 outputs information required for the judgment. Thus, the optical test apparatus 10 of the present embodiment can perform internal inspection of the object 40 without contact, and detect and acquire the presence/absence of the refractive index distribution in the object 40 as the information concerning the internal physical quantities of the object 40.

It is to be noted that when the first light direction (the vector eA) can be acquired as described above, the first light direction (the vector eA) may be calculated or acquired on the basis of the output of the photodetector 13 in the standard state. Here, the standard state is a state where the refractive index distribution 52 is not present in the object 40, a state where the object 40 is not present in the test region 30, or the like. Needless to say, it can be considered that it is known whether or not the refractive index distribution 52 is present in the object 40 and, for example, it can be considered that the internal inspection of the object 40 is performed when pressure, temperature, stress or the like is applied to the object 40. Alternatively, the first light direction (the vector eA) may be calculated or acquired on the basis of the output of the probe beam generating unit 12, or may be beforehand calculated in accordance with the constitution of the probe beam generating unit 12, to be recorded in the optical test apparatus 10 or the like.

Furthermore, when the first light direction (the vector eA) can be acquired as described above, the photodetector 13 of the present embodiment further acquires information concerning the time-series change of the passing light direction to output the information to the processing circuit 14. On the basis of the time-series change, the processing circuit 14 may update the standard light direction. For example, the processing circuit 14 compares the current passing light direction with the acquired passing light direction that is used as the standard light direction. As a result of the comparison, when the passing light direction is different from the standard light direction, it is judged that there is the change of the refractive index distribution 52. By such comparison, the optical test apparatus 10 of the present embodiment can perform the internal inspection of the object 40 without contact, and detect and acquire presence/absence of the change of the refractive index distribution in the object 40, as the information concerning the internal physical quantities of the object 40.

Next, in the optical test apparatus 10 according to the present embodiment, there is considered an example where it can be guaranteed that at least the first light direction (the vector eA) is constant. In this case, the processing circuit 14 acquires the time-series change of the second light direction (the vector eB) of the received probe beam 51 which has passed through the object 40. The processing circuit 14 acquires the second light direction in the standard state as the standard light direction from the time-series change. Here, the standard state is a state where the refractive index distribution on the light path is constant or considered to be constant. The standard light direction can be acquired, for example, when it is known that the refractive index distribution is constant, for example, before an experiment is started, or when displacement of the passing light direction (the incident angle) is smaller than a specific threshold value in a predetermined time. Afterward, the processing circuit 14 acquires the second light direction as the passing light direction and compares the direction with the standard light direction. The processing circuit 14 acquires information concerning the change of the refractive index distribution 52 on the light path of the probe beam 51 (the passed light) on the basis of a result of the comparison of the passing light direction with the standard light direction. When the passing light direction is different from the standard light direction, the processing circuit 14 judges that the refractive index distribution 52 on the light path of the probe beam 51 (the passed light) has changed. In this way, the optical test apparatus 10 of the present embodiment can perform the internal inspection of the object 40 without contact, and detect and acquire the change of the refractive index distribution in the object 40 as the information concerning the internal physical quantities of the object 40 on the basis of the time-series change of the second light direction (the passing light direction).

Additionally, in the case that it can be judged that the refractive index distribution 52 is not present on the light path when the standard light direction is acquired, the presence/absence of the refractive index distribution 52 on the light path of the probe beam 51 (the passed light) can be acquired in the same manner as in the above-mentioned case where the first light direction (the vector eA) can be acquired. In other words, the optical test apparatus 10 of the present embodiment can perform the internal inspection of the object 40 without contact, and detect and acquire the presence/absence of the refractive index distribution in the object 40 as the information concerning the internal physical quantities of the object 40 on the basis of the time-series change of the second light direction (the passing light direction).

It is to be noted that there has been described the example where the first light direction or the second light direction (the passing light direction) in the standard state is used as the standard light direction, but the present embodiment is not limited to this example. For example, the standard light direction may be the optical axis direction of the photodetector 13 or a user's arbitrary direction, and in any case, an effect similar to the above-mentioned effect is obtainable. In this case, a relation between the standard light direction and the first light direction may only be known.

As described above, an object for which the optical test apparatus 10 according to the present embodiment detects the presence/absence or change of the refractive index distribution 52, i.e., the object 40 may be the gas, the liquid, or the solid. The refractive index of the gas can change, for example, in accordance with a type of gas and a density thereof. Furthermore, the density of the gas can change in accordance with a temperature of the gas and a pressure thereof as described in a state equation for the gas. Additionally, the density of the gas can change when different gas types are mixed, i.e., in accordance with a ratio of each component constituting the gas. In addition, a refractive index of the liquid or the solid can change in accordance with a liquid or solid type, internal stress, strain, density, temperature, or pressure, or any combination of these parameters. Furthermore, the refractive index of the liquid or the solid can change in accordance with a ratio of each component constituting the liquid or the solid. Additionally, a pressure wave such as an acoustic wave which propagates through the gas, the liquid or the solid causes increase or decrease of the density in a propagating medium, and hence, the refractive index can be generated in the medium. Therefore, the information concerning the internal physical quantities of the object 40 which is acquired by the optical test apparatus 10 of the present embodiment is not limited to the presence/absence or change of the refractive index distribution, and includes information concerning a physical quantity such as the above-mentioned density which has an influence on the refractive index in the object 40.

Furthermore, the object in which the presence/absence or change of the refractive index distribution is detected by the optical test apparatus 10 according to the present embodiment may be a liquid or a solid which moves in a gas, the gas or the solid which moves in the liquid, or the gas or the liquid which moves in the solid. That is, the optical test apparatus 10 of the present embodiment can detect and acquire the presence/absence of the object 40 of the substance through which the probe beam 51 is passable or transmittable and in which the refractive index of the probe beam 51 can change, in the test region 30.

(Modification Concerning Acquisition of Light Direction)

It is to be noted that the acquisition of the second light direction (the vector eB) when the probe beam 51 enters the photodetector 13 is not limited to the method described above in the embodiment.

For example, the photodetector 13 may be constituted so that a light receiving surface including light receiving elements is spherically disposed. In this case, among the light receiving elements of the photodetector 13, the light receiving element which receives the probe beam 51 outputs the light receiving signal to the processing circuit 14. Then, the processing circuit 14 calculates the second light direction (the vector eB) on the basis of positional information of the disposed light receiving element. Also according to this constitution, an effect similar to that of the above-mentioned embodiment is obtainable. It is to be noted that when the light receiving element is capable of outputting a light receiving position, a light receiving surface of the light receiving element may be similarly spherically constituted. Needless to say, for the purpose of improving a detection accuracy, the spherical light receiving surfaces may be arranged in the optical axis direction of the photodetector 13.

For example, when the first light direction (the vector eA) is constant, the photodetector 13 may be a luminance sensor or the like which is configured to detect a luminance distribution of a plane orthogonal to the vector eA. In this case, for example, a light diameter of the probe beam 51 may be enlarged in accordance with a light receiving area of the luminance sensor, or a light receiving optical system. Also in this constitution, when the refractive index distribution is generated on the light path and the light direction changes, the luminance distribution is generated in the light receiving signal, and hence, an effect similar to that of the above-mentioned embodiment is obtainable.

For example, when the first light direction (the vector eA) during the emission of the probe beam 51 is known, the photodetector 13 only detects whether or not the light of the first light direction is received. Specifically, the processing circuit 14 acquires the first light direction as the standard light direction. Furthermore, the processing circuit 14 acquires the presence/absence of the reception of the probe beam 51 in the standard light direction as the information concerning the passing light direction, from the photodetector 13. When the photodetector 13 detects the probe beam 51, the processing circuit 14 judges that the passing light direction is the same as the standard light direction and judges that the refractive index distribution is not present. Also according to this constitution, there is obtainable the effect that the presence/absence of the refractive index distribution can be detected and acquired in the same manner as in the above-mentioned embodiment.

For example, when a part of the probe beam 51 (the passed light) is scattered on the light path, a light position or the light direction can occasionally be acquired on the basis of the scattered light on the light path of the probe beam 51 (the passed light). In this case, for example, the photodetector 13 receives the scattered light, and acquires an image including the light path of the passed light to enter the photodetector 13 as information concerning the light direction. The processing circuit 14 subjects the image to image processing and acquires the passing light direction on the basis of a result of the image processing and information concerning an imaging direction of the photodetector 13. It is to be noted that the photodetector 13 may comprise a scattering medium to the probe beam 51 in an imaging range.

Modification of First Embodiment

Figure 3:
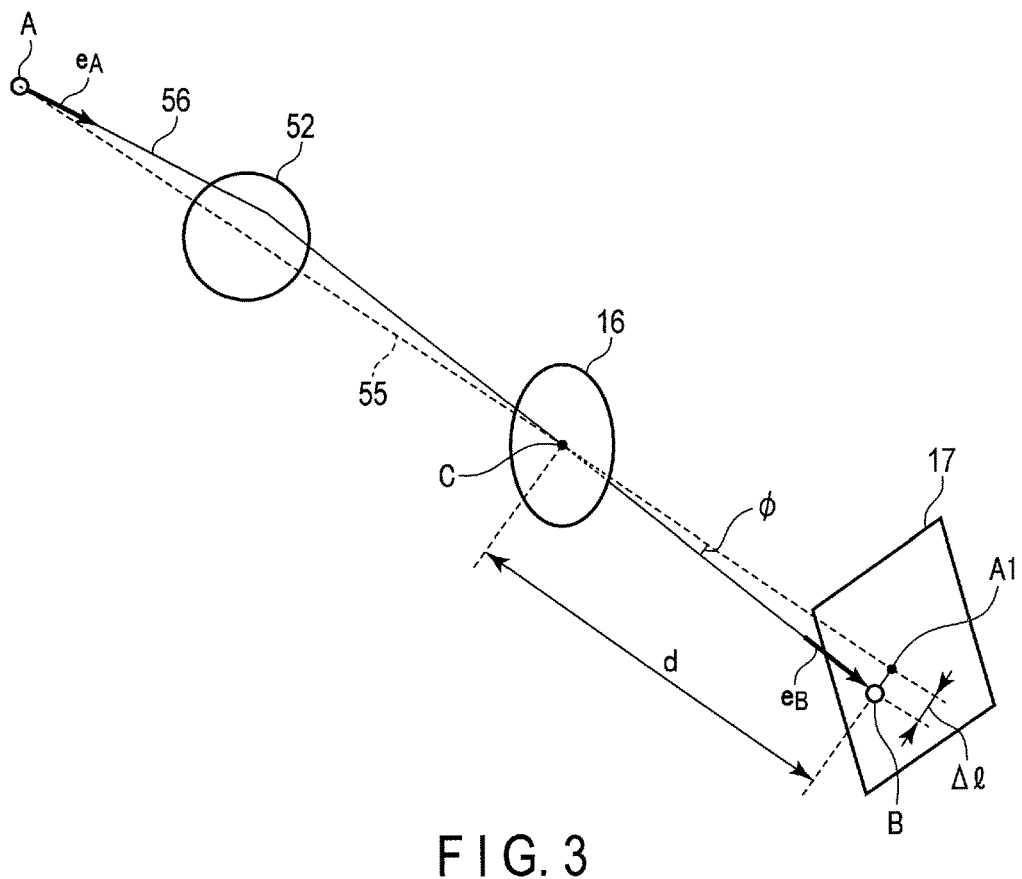
FIG. 3 is a schematic diagram to explain a measurement principle of an optical test apparatus according to a modification of the first embodiment.

In the first embodiment, the description has been made as to the optical test apparatus 10 in which the photodetector 13 measures the second light direction (the vector eB) of the probe beam 51 to acquire the information concerning the internal physical quantities of the object 40, but a measuring method is not limited to the above-mentioned method. FIG. 3 shows a schematic diagram to explain a measurement principle of an optical test apparatus 10 according to the present modification. Hereinafter, description will be made as to the optical test apparatus 10 of the present modification in detail with reference to the drawings.

As shown in FIG. 3, a photodetector 13 according to the present modification comprises a light receiving optical system 16 which emits entered light from a light position corresponding to a light direction of the light when the light enters the system, and an imaging element including a light receiving surface which detects the light position. The light receiving optical system 16 comprises an image forming lens to form an image of the light emitted from a position A on an imaging surface 17 of the imaging element. Here, for the sake of simplicity, description is made as to an example where an optical axis of the image forming lens matches an optical axis of the photodetector 13 and the imaging surface 17 is orthogonal to these optical axes. Here, a distance d between the image forming lens and the imaging surface 17 is known.

When a refractive index distribution 52 is not present on a light path, a light path of probe beam 51 forms a straight line as described above with reference to FIG. 2. For example, it is considered that the light direction during the emission of the probe beam 51 from a probe beam generating unit 12 is an optical axis direction of the image forming lens and that an emission end of the probe beam generating unit 12 is present on the optical axis. In this case, as shown by a broken line 55 in FIG. 3, the probe beam 51 emitted from the position A passes a point C on the image forming lens and enters a point A1 on the imaging surface 17. Here, the point C is a point on the optical axis of the image forming lens, and the light path which passes the position A, the point C and the point A1 forms the straight line.

On the other hand, when the refractive index distribution 52 is present on the light path, the light direction of the probe beam 51 emitted from the position A is changed during passing of the light through a region where the refractive index distribution 52 is present, for example, as shown by a solid line 56 in FIG. 3. Therefore, the light direction (a vector eB) of the probe beam 51 when the light enters the imaging surface 17 has an inclination to the optical axis of the image forming lens. Therefore, an incident position of the probe beam 51 into the imaging surface 17 which is shown as a position B in FIG. 3 changes in accordance with an inclination angle $\phi$ that is an angle formed by the vector eB and the optical axis.

According to this constitution, the optical test apparatus 10 according to the present modification can calculate the inclination angle $\phi$ as $\phi = \arctan(\Delta l/d)$, in which $\Delta 1$ is a distance between the point A1 and the position B.

Thus, the optical test apparatus 10 according to the present modification can acquire a second light direction (a passing light direction) of the probe beam 51 which enters a photodetector 13 on the basis of information concerning the incident position of the probe beam 51 into the imaging surface 17 (the light receiving surface). That is, the optical test apparatus 10 of the present modification has advantages similar to those of the optical test apparatus 10 of the first embodiment.

It is to be noted that in the optical test apparatus 10 of the present modification, it can be considered that, when the position A is disposed sufficiently away from the image forming lens, the light direction of the probe beam 51 emitted from the position A to reach the image forming lens is parallel to the optical axis of the image forming lens. Specifically, when a first light direction (a vector eA) of the emitted probe beam 51 corresponds to the light direction, the direction is usable as known information, though the direction is not measured. In this case, the processing circuit 14 acquires the optical axis direction as a standard light direction.

Here, for example, it is considered that a refractive index of an ambient environment at the position A which is sufficiently away from the image forming lens is equal to that at the position B on the imaging surface 17. At this time, the second term of the right side of Equation (4) is eA. Specifically, in the optical test apparatus 10 of the present modification, when a second light direction (the vector eB) of the probe beam 51 at the position B is acquired as described above, information concerning the refractive index distribution 52 on the light path can be acquired as represented by the first term of Equation (4), because there is known the first light direction (the vector eA) in an initial period when the probe beam 51 is emitted.

It is to be noted that in the optical test apparatus 10 according to the present modification, an effect similar to the above-mentioned effect of the embodiment is obtainable, even when the light direction is not calculated. In this case, the photodetector 13 outputs information concerning a passing light position as information concerning the passing light direction to the processing circuit 14. Here, the light position may be calculated in the photodetector 13 or the processing circuit 14. The processing circuit 14 acquires a standard light position corresponding to the standard light direction as information concerning the standard light direction. The standard light position may be beforehand measured and recorded in the optical test apparatus 10, or the passing light position corresponding to the passing light direction in a standard state may be acquired and used. The processing circuit 14 compares the passing light position (the information concerning the passing light direction) with the standard light position (the information concerning the standard light direction). The processing circuit 14 judges that the refractive index distribution is present on the light path of the passed light (the probe beam 51), when the passing light position is different from the standard light position. In this way, the optical test apparatus 10 of the present modification does not calculate the light direction, but performs internal inspection of the object 40 without contact, and detects and acquires the presence/absence or change of the refractive index distribution in the object 40 as information concerning internal physical quantities of the object 40.

It is to be noted that in the optical test apparatus 10 according to the above-mentioned embodiment or modification, light including wavelengths may be used as the probe beam 51. Similarly, the probe beam 51 may be the light including the wavelengths. As described above, the refractive index varies in accordance with the internal density or the like of the object 40, but it is known that even in the same object 40 having the same state, the refractive index varies in accordance with a wavelength of an electromagnetic wave for use as the probe beam 51. It can be considered that wavelength dependency of the refractive index distribution 52 varies with substances. That is, in the optical test apparatus 10 in which the light including the wavelengths is used as the probe beam 51, the information concerning the refractive index distribution can be acquired with respect to each of the wavelengths of the probe beam 51. In this case, the photodetector 13 is configured to output the information concerning the light direction with respect to each of at least two wavelengths. In the optical test apparatus 10, the dependency of the refractive index distribution of the passed light (the probe beam 51) on the wavelength can be acquired. The optical test apparatus 10 has the effect that the substance (the object 40) which is present in the test region 30 can be specified or the substance which can be present in the test region 30 can be limited, on the basis of the wavelength dependency.

The optical test apparatus 10 according to the present embodiment can be concluded as follows.

The optical test apparatus 10 according to the present embodiment comprises the photodetector 13 which outputs, as the light receiving signal, the information concerning the light direction of the received light (e.g., the probe beam 51), and the processing circuit 14 which processes the light receiving signal to acquire the information concerning the standard light direction as the standard and the information concerning the passing light direction of the passed light which has passed through the object 40, compares the information concerning the passing light direction with the information concerning the standard light direction, and on the basis of the results of the comparison, acquires the information concerning the internal physical quantities of the object 40.

According to this constitution, when the first light direction is acquired as the standard light direction from the outside, and when the refractive index distribution is not present in the object 40 and the first light direction is measured and acquired as the standard light direction, the presence/absence of the refractive index distribution 52 in the object 40 can be detected and acquired without contact, as the information concerning the internal physical quantities of the object 40 from the comparison of the measured passing light direction with the standard light direction.

Furthermore, according to this constitution, when it is guaranteed that the first light direction is constant, the presence/absence of the change of the refractive index distribution 52 in the object 40 can be detected and acquired without contact, as the information concerning the internal physical quantities of the object 40 from the measured time-series change of the passing light direction.

An optical test method according to the present embodiment includes receiving the passed light (the probe beam 51) which has passed through the object 40, acquiring the information concerning the standard light direction that is the standard as standard light information, acquiring the information concerning the passing light direction of the received passed light (the probe beam 51) as passing light information, comparing the standard light information with the passing light information, and on the basis of results of the comparison, acquiring the information concerning the internal physical quantities of the object 40. Here, the standard light information is the standard light direction, an output value of the photodetector 13 which can be converted to the standard light direction, the standard light position corresponding to the standard light direction, an output value of the photodetector 13 which can be converted to the standard light position corresponding to the standard light direction, or the like. Furthermore, the passing light information is the passing light direction, an output value of the photodetector 13 which can be converted to the passing light direction, the passing light position corresponding to the passing light direction, an output value of the photodetector 13 which can be converted to the passing light position corresponding to the passing light direction, or the like. According to this method, the above-mentioned effect is obtainable.

The optical test apparatus 10 according to the present embodiment further comprises the probe beam generating unit 12 which emits, in the standard light direction, as the light, the probe beam 51 having a wavelength transmittable (or passable) through the object 40. It is to be noted that the probe beam generating unit 12 is an optical element such as a filter or a collimator. Furthermore, the probe beam generating unit 12 may further comprise the light source. According to this constitution, in addition to the above effect, there is the effect that the first light direction of the known information is usable as the standard light direction and it can be easily guaranteed that the first light direction is constant. Furthermore, the wavelength of the probe beam 51 which is suitable for the object 40 is selectable.

The processing circuit 14 of the optical test apparatus 10 according to the present embodiment acquires the time-series change of the information concerning the light direction, and acquires the information concerning the light direction in the standard state as the information concerning the standard light direction. According to this constitution, an effect similar to the above-mentioned effect is obtainable only on the basis of the output of the photodetector 13.

The photodetector 13 of the optical test apparatus 10 according to the present embodiment comprises the light receiving optical system 16 which acquires the light position of the light (the probe beam 51) as the light position corresponding to the light direction, and the light receiving surface (the imaging surface 17) configured to detect the light position, the information concerning the standard light direction is the standard light position corresponding to the standard light direction, and the information concerning the passing light direction is the passing light position corresponding to the passing light direction. According to this constitution, in addition to the above effect, there is the effect that the presence/absence or change of the refractive index distribution in the object 40 can be detected and acquired without contact, only on the basis of the information concerning the light position without calculating the light direction. Furthermore, according to this constitution, when it is considered that the emission end of the probe beam generating unit 12 is disposed sufficiently away from the light receiving optical system 16, it can be considered that the first light direction is parallel to the optical axis of the light receiving optical system 16. That is, the first light direction can be acquired as the information concerning the standard light direction without measuring the direction.

The photodetector 13 of the optical test apparatus 10 according to the present embodiment outputs the information concerning the light direction with respect to each of at least two wavelengths, the processing circuit 14 acquires the wavelength dependency concerning the refractive index distribution 52 on the light path of the passed light (the probe beam 51) in the object 40 on the basis of the above results, and the processing circuit acquires the information concerning the substance constituting the object 40 as the information concerning the internal physical quantities of the object 40 on the basis of the wavelength dependency. According to this constitution, in addition to the above effect, there is the effect that the substance constituting the object 40 can be specified without contact.

Second Embodiment

Hereinafter, description will be made as to an optical test apparatus 10 according to the present embodiment in detail with reference to the drawings. Here, differences from the first embodiment are mainly described, and the same parts are denoted with the same reference signs to omit description thereof.

Figure 4:
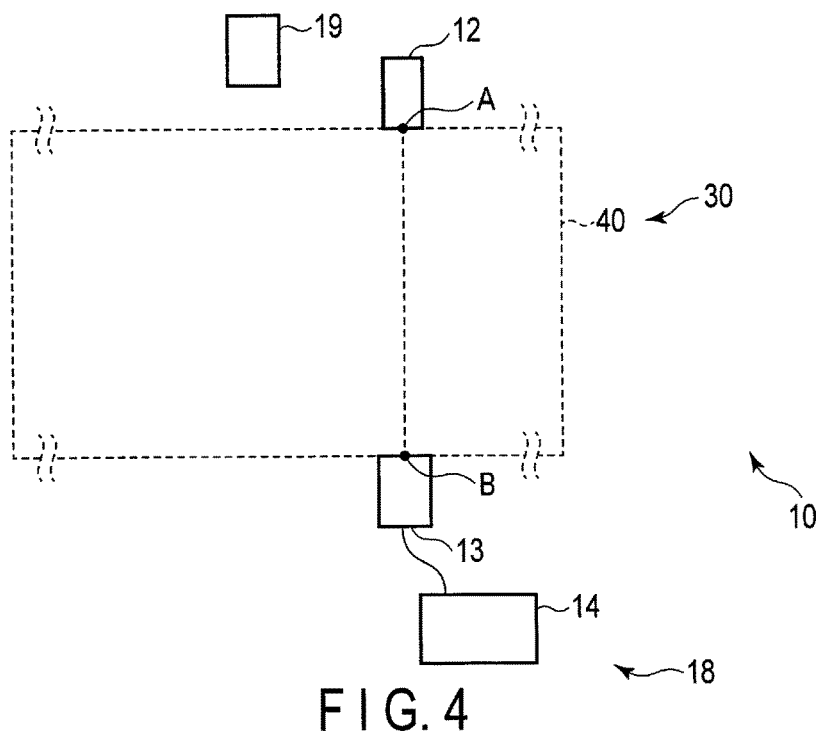
FIG. 4 is a schematic diagram showing a constitutional example of an optical test apparatus according to a second embodiment.

Initially, description is made as to a constitution of the optical test apparatus 10 according to the present embodiment. FIG. 4 is a schematic diagram schematically showing a constitutional example of the optical test apparatus 10 according to the present embodiment. FIG. 4 schematically shows a test region 30 in addition to the constitutional example of the optical test apparatus 10.

As shown in FIG. 4, the optical test apparatus 10 according to the present embodiment further comprises an acoustic wave generating unit 19. The acoustic wave generating unit 19 generates and propagates an acoustic plane wave (an elastic wave) in an object 40. It is to be noted that the acoustic plane wave (an acoustic wave) may be an ultrasonic wave.

It is to be noted that the acoustic wave generating unit 19 according to the present embodiment is constituted to propagate the acoustic plane wave along a light path of probe beam 51 emitted by a probe beam generating unit 12 according to the present embodiment, in the object 40. At this time, a wave front of the acoustic plane wave is orthogonal to a line segment connecting an emission end of the probe beam generating unit 12 to an entrance end of a photodetector 13. Furthermore, the acoustic wave generating unit 19 can generate the acoustic plane wave to generate a diffracted wave in the object 40 from interference of the wave with a refractive index distribution on a propagation path. Here, the diffracted wave can change a refractive index distribution on the light path of the probe beam 51.

It is to be noted that the object 40 according to the present embodiment may be a gas, a liquid, a solid, or a mixture of at least two of the gas, the liquid and the solid.

For example, when the object 40 is the gas, the acoustic wave generating unit 19 generates the acoustic plane wave in the gas (the object 40) which is present in the test region 30. In this case, the acoustic wave generating unit 19 is, for example, a plane wave speaker, a flat panel speaker or the like. Furthermore, the emission end of the probe beam 51 in the probe beam generating unit 12 is defined as a position A and the entrance end of the probe beam 51 in the photodetector 13 is defined as a position B.

For example, when the object 40 is the liquid or the solid, the acoustic wave generating unit 19 generates the acoustic plane wave (the elastic wave) in the object 40 which is present in the test region 30. In this case, the acoustic wave generating unit 19 may be a laser oscillator which irradiates the object 40 with pump beam (excitation light) to generate the elastic wave in the object 40. Furthermore, the pump beam may be short pulse laser light. It is to be noted that a wavelength of the pump beam is a wavelength included in an absorption wavelength of the object 40. Additionally, an end of the object 40 on the side of the probe beam generating unit 12 on the light path of the probe beam 51 is defined as the position A and the other end (an end of the object on the side of the photodetector 13) is defined as the position B.

Hereinafter, description will be made as to an example where the object 40 is the gas and the acoustic plane wave is the elastic wave which propagates in the gas as shown in FIG. 4. That is, in the present embodiment, there is considered a light direction on the light path of the probe beam 51 which is emitted from the position A and can be entered to the position B.

Figure 5:
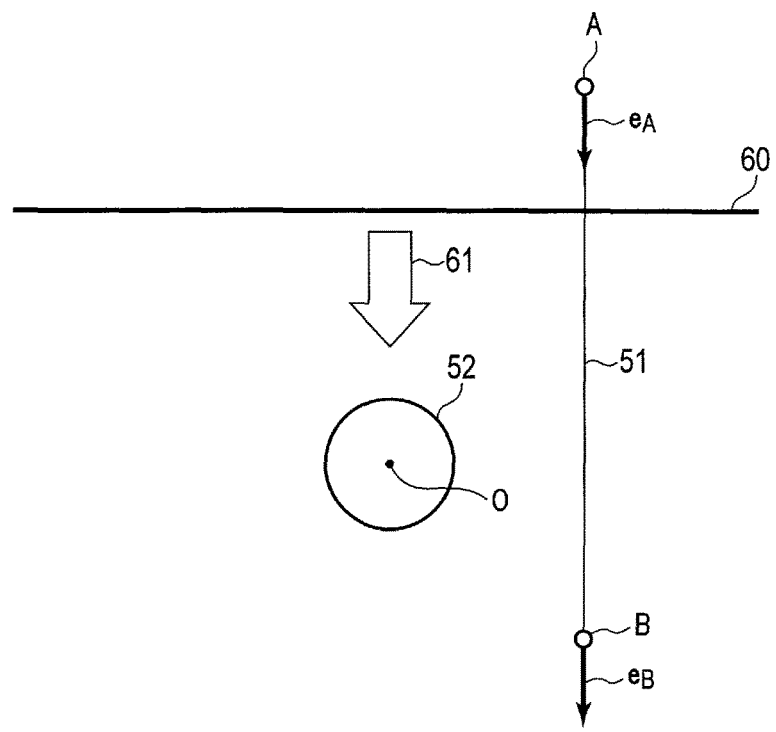
FIG. 5 is a schematic diagram to explain a measurement principle of the optical test apparatus according to the second embodiment, and shows a state before an acoustic plane wave reaches a refractive index distribution.
Figure 6:
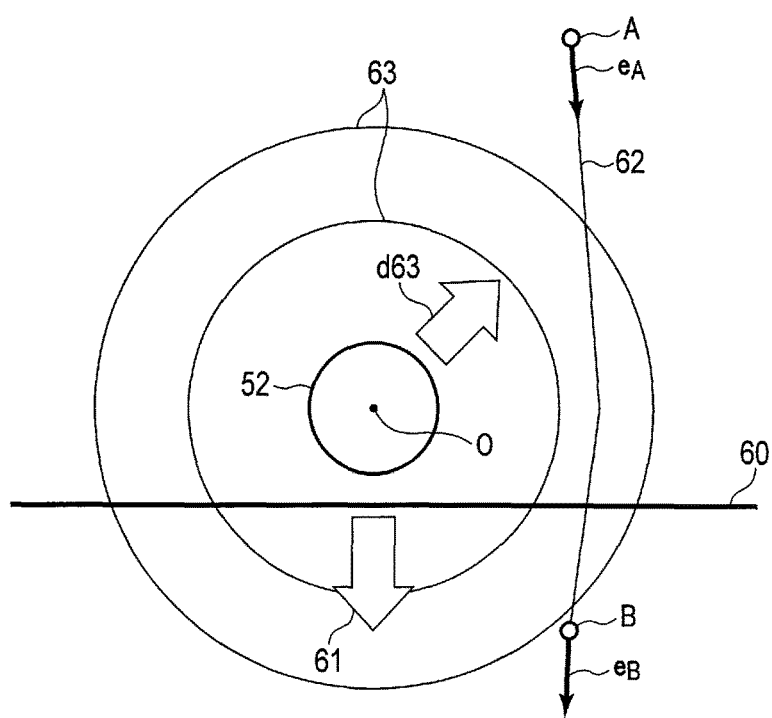
FIG. 6 is a schematic diagram to explain a measurement principle of the optical test apparatus according to the second embodiment, and shows a state after the acoustic plane wave reaches a refractive index distribution.

Next, description will be made as to an operation of the optical test apparatus 10 according to the present embodiment with reference to FIG. 5 and FIG. 6. FIG. 5 is a schematic diagram to explain a measurement principle of the optical test apparatus 10 according to the present embodiment, and shows a state before an acoustic plane wave 60 reaches a refractive index distribution 52. Furthermore, FIG. 6 is a schematic diagram to explain a measurement principle of the optical test apparatus 10 according to the present embodiment, and shows a state after the acoustic plane wave 60 further propagates from the state shown in FIG. 5 in a propagating direction 61 and the acoustic plane wave 60 reaches the refractive index distribution 52.

Here, for example, it is considered that a density distribution is present in the vicinity of a center of the object 40. Additionally, it is considered that the density is constant in a region other than the vicinity of the center. At this time, in the object 40, the refractive index distribution 52 is present in accordance with the density distribution.

It is to be noted that in the following description, for the sake of simplicity, it is considered that a refractive index n(rB) at the position B is the same as a refractive index n(rA) at the position A. However, the present technology is established also when the refractive index n(rB) at the position B is different from the refractive index n(rA) at the position A as described above.

The probe beam generating unit 12 according to the present embodiment emits the probe beam 51 from the position A or emits the light so that the light passes the position A. Then, the photodetector 13 receives the probe beam 51 which is emitted from the position A or which has passed the position A. Here, the light path of the probe beam 51 forms a straight line which passes the position A and the position B, when the refractive index distribution is not present between the position A and the position B.

The acoustic wave generating unit 19 according to the present embodiment generates the acoustic plane wave 60 in the object 40, along the straight line which passes the position A and the position B, i.e., in the propagating direction 61. That is, the wave front of the acoustic plane wave 60 is orthogonal to the straight line which passes the position A and the position B. Here, a direction from the position A toward the position B is defined as a Z direction, and a unit direction vector in the Z direction is defined as a vector eZ.

Here, initially, there is considered the state before the acoustic plane wave 60 reaches the refractive index distribution 52 as shown in FIG. 5. At this time, it is assumed that the refractive index n(rA) at the position A is the same as the refractive index n(rB) at the position B, the refractive index distribution 52 is not present between the position A and the position B, and hence, Equation (4) is developed as follows.

$$\vec{e}_B = \vec{e}_A \quad \text{Equation (6).}$$

Therefore, a first light direction at the position A matches a second light direction at the position B and the light direction does not change between the position A and the position B.

Next, there is considered the state after the acoustic plane wave 60 further propagates from the state shown in FIG. 5 in the propagating direction 61 and the acoustic plane wave 60 reaches the refractive index distribution 52 as shown in FIG. 6. At this time, a diffracted wave 63 is generated from interference of the acoustic plane wave 60 with the refractive index distribution 52.

The diffracted wave 63 generated in this way propagates, for example, from a central position O of the refractive index distribution 52 in a propagating direction d63. Here, the propagating direction d63 is a radial direction based on the central position O. Afterward, the diffracted wave 63 which propagates in the propagating direction d63 reaches the light path of the probe beam 51 and interferes with the probe beam 51. At this time, Equation (4) is developed as follows.

$$\vec{e}_B = \frac{1}{n(\vec{r}_B)} \int_A^B ds \left[ \frac{\partial n(\vec{r})}{\partial r} \vec{e}_r \right] + \vec{e}_A. \quad \text{Equation (7)}$$

Here, a vector er is a unit vector of the radial direction based on the central position O, and grad<n(r)er>in the first term of the right side of Equation (7) is a gradient of the refractive index on the light path which is generated by the diffracted wave 63. A vector quantity represented by the first term of the right side of Equation (7) is directed in the radial direction when a differential of the refractive index of an integrand in the first term in the radial direction is positive, and the vector quantity is directed in a direction opposite to the radial direction when the differential is negative. That is, when the refractive index heightens along the radial direction, the first term represents the vector quantity directed in the radial direction. Consequently, it is seen that the light direction is bent along the radial direction to heighten the refractive index. That is, the light direction changes between the position A and the position B. In other words, the change of the light direction depends on a positional relation between the light path of the probe beam 51 and a position at which the diffracted wave 63 is generated. Specifically, information concerning the change of the second light direction (a passing light direction) of the probe beam 51 (passed light) at the entrance end of the photodetector 13 includes information concerning a position of the refractive index distribution 52 in the object 40.

As described above, the acoustic wave generating unit 19 of the optical test apparatus 10 according to the present embodiment generates the acoustic plane wave 60 in the object 40. The acoustic plane wave 60 propagates in the object 40 and interferes with the refractive index distribution 52 on the propagation path to generate the diffracted wave 63. The diffracted wave 63 changes the refractive index or the refractive index distribution on the light path of the probe beam 51 (the passed light). Here, in the optical test apparatus 10 of the present embodiment, information concerning a standard light direction and information concerning the passing light direction of the probe beam 51 (the passed light) are acquired and compared in the same manner as in the optical test apparatus 10 of the first embodiment. Specifically, in the optical test apparatus 10 of the present embodiment, presence/absence or change of the refractive index distribution 52 on the propagation path of the acoustic plane wave 60 can be acquired as presence/absence or change of the refractive index distribution on the light path of the probe beam 51. That is, in the optical test apparatus 10 of the present embodiment, the presence/absence or the change of the refractive index distribution which is derived from a density distribution or the like on the propagation path of the acoustic plane wave 60 can be detected and acquired without contact in the object 40. Furthermore, as described above, a region where the optical test apparatus 10 of the present embodiment can detect the presence/absence or the change of the refractive index distribution is not limited to a region on the light path of the probe beam 51. Specifically, the optical test apparatus 10 of the present embodiment comprises the acoustic wave generating unit 19, and can therefore detect and acquire the presence/absence or the change of the refractive index distribution which is not present on the light path of the probe beam 51.

First Modification of Second Embodiment

In the second embodiment, there has been described the example of the optical test apparatus 10 in which when the refractive index distribution is generated by the density distribution, the presence/absence or the change of the density distribution in the object 40 is detected and acquired, but the present embodiment is not limited to this example.

For example, when a detection object of the optical test apparatus 10, i.e., an object 40 is a gas, a refractive index in the object 40 can change in accordance with a type of gas that is the object 40, its temperature, pressure, density or the like. Furthermore, for example, when the object 40 is a liquid or a solid, the refractive index in the object 40 can change in accordance with a type of object 40, its temperature, internal stress, strain, density or the like. Specifically, information concerning internal physical quantities of the object 40 which can be acquired in the optical test apparatus 10 of the present embodiment includes information concerning a physical quantity which can vary the refractive index in the object 40. The optical test apparatus 10 of the present modification has the effect that information concerning a passing light direction of the probe beam 51 or information concerning a time-series change of the passing light direction can be acquired to detect and acquire, without contact, information concerning the physical quantity on a propagation path of an acoustic plane wave 60 in the object 40.

It is to be noted that a change of the physical quantity which contributes to the change of the refractive index in the object 40 may be generated in a part of the object 40 or the whole object 40 as described above. In any case, according to the optical test apparatus 10 of the present modification, the change of the physical quantity in the object 40 can be detected and acquired without contact.

Second Modification of Second Embodiment

The above-mentioned measurement may be performed by changing a relative position between an object 40 and a light path of probe beam 51. For example, the optical test apparatus 10 of the above-mentioned embodiment can acquire the change of the second light direction to detect and acquire the direction in which the refractive index distribution 52 is present to the light path. Specifically, according to an optical test apparatus 10 of the present modification, information concerning a second light direction (a passing light direction) or a time-series change of the information concerning the passing light direction is acquired at a relative position between the object 40 and each of the light paths of the probe beam 51, thereby producing the effect that a position of a refractive index distribution can be estimated. Alternatively, there is similarly considered an optical test apparatus 10 in which a shape of a refractive index distribution can be reconstructed.

The optical test apparatus 10 according to the present embodiment can be concluded as follows.

The optical test apparatus 10 according to the present embodiment further comprises the probe beam generating unit 12 which emits, in the standard light direction, as the light, the probe beam 51 including the wavelength transmittable (passable) through the object 40, and the acoustic wave generating unit 19 configured to generate the acoustic wave (the acoustic plane wave 60) in the object 40, and configured to generate the diffracted wave 63 which changes the refractive index distribution on the light path of the passed light (the probe beam 51) from the interference of the wave with the refractive index distribution 52 on the propagation path of the acoustic wave (the acoustic plane wave 60) in the object 40, and the processing circuit 14 acquires the presence/absence or change of the refractive index distribution 52 on the propagation path of the acoustic wave (the acoustic plane wave 60) in the object 40 as the information concerning the internal physical quantities of the object 40. According to this constitution, the presence/absence or change of the refractive index distribution 52 on the path through which the acoustic plane wave 60 passes in the object 40 can be detected and acquired without contact. In other words, the detectable refractive index distribution 52 is not limited to the refractive index distribution 52 which is present on the light path of the probe beam 51 (the passed light). Furthermore, the information concerning the change of the second light direction (the passing light direction) of the probe beam 51 (the passed light) includes information concerning a relative position between the refractive index distribution 52 in the object 40 and the light path of the probe beam 51 (the passed light).

The acoustic wave generating unit 19 of the optical test apparatus 10 according to the present embodiment propagates the acoustic wave (the acoustic plane wave 60) along the straight line connecting the probe beam generating unit 12 to the photodetector 13. According to this constitution, the interference of the acoustic plane wave 60 with the probe beam 51 can decrease, and hence, the effect that a detection accuracy can improve is obtainable in addition to the above-mentioned effect.

In the optical test apparatus 10 according to the present embodiment, the wave front of the acoustic wave (the acoustic plane wave 60) is substantially orthogonal to the straight line connecting the probe beam generating unit 12 to the photodetector 13. Thus, in the optical test apparatus 10 according to the present embodiment, the straight line is substantially parallel to the propagating direction 61 of the acoustic wave (the acoustic plane wave 60). According to this constitution, the interference of the acoustic plane wave 60 with the probe beam 51 (the passed light) can further decrease, and hence, the effect that the detection accuracy can further improve is obtainable in addition to the above-mentioned effect.

The acoustic wave generating unit 19 of the optical test apparatus 10 according to the present embodiment emits the short pulse laser light toward the object 40, to generate the acoustic wave (the acoustic plane wave 60). According to this constitution, for example, when the object 40 is the solid, a steep elastic wave (the acoustic plane wave 60) can be generated in the vicinity of a surface 41 of the object 40, and hence, the improvement of the detection accuracy is achievable.

Third Embodiment

Hereinafter, description will be made as to an optical test apparatus 10 according to the present embodiment in detail with reference to the drawings. Here, differences from the second embodiment are mainly described, and the same parts are denoted with the same reference signs to omit description thereof.

Figure 7:
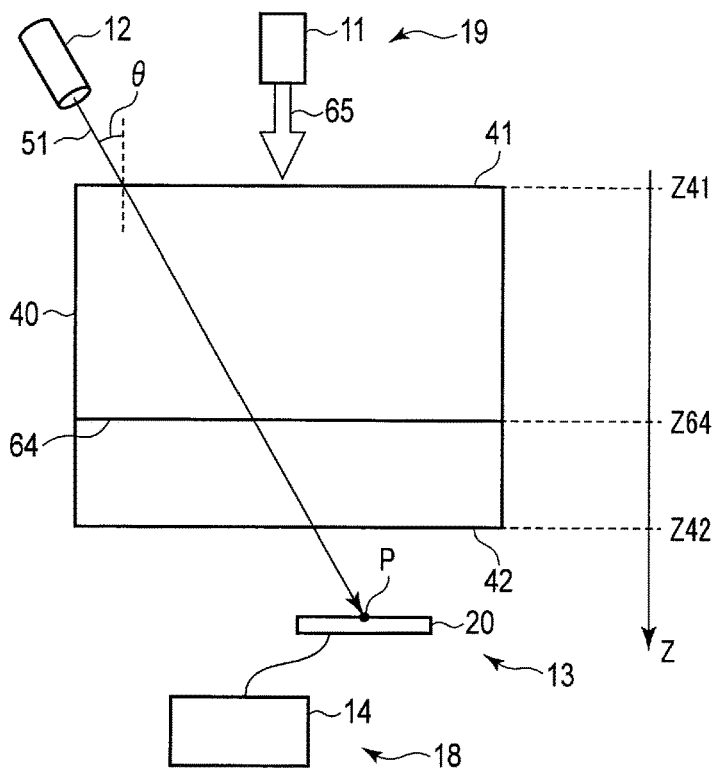
FIG. 7 is a schematic diagram showing a constitutional example of an optical test apparatus according to a third embodiment.

FIG. 7 is a schematic diagram schematically showing a constitutional example of the optical test apparatus 10 according to the present embodiment. FIG. 7 also shows a schematic diagram showing a cross section of an inspection sample (an object 40). In the present embodiment, the description is made as to an example where the object 40 is a solid. It is to be noted that there are not any restrictions on a solid sample for use as the object 40, and examples of the sample include metals (including alloys) such as stainless steel, Au, Al, Cu, W and Ti, and non-metals such as carbon and amorphous carbon. Furthermore, the object 40 may be a semiconductor of Si, SiC or the like, or a resin such as acryl or carbonate. Additionally, the object 40 may comprise a structure of a multilayered film or the like therein.

Hereinafter, in the present embodiment, description will be made as to an example where the object 40 has an interface 64 therein as shown in FIG. 7. Furthermore, in the following description, as shown in FIG. 7, a depth direction of the object 40 is defined as a Z direction, a direction from a surface 41 toward a back surface 42 of the object 40 is defined as a Z+ direction, and a direction from the back surface 42 toward the surface 41 of the object 40 is defined as a Z− direction. Here, a position of the surface 41 of the object 40 in the Z direction is denoted with Z41, a position of the back surface 42 of the object 40 in the Z direction is denoted with Z42, and a position of the interface 64 in the Z direction is denoted with Z64.

As shown in FIG. 7, the optical test apparatus 10 according to the present embodiment comprises an pump beam generating unit 11. The pump beam generating unit 11 of the present embodiment generates, in the object 40, an elastic wave (an acoustic plane wave) which propagates in the object 40 in the Z direction. That is, the pump beam generating unit 11 of the present embodiment is included in an acoustic wave generating unit 19 according to the second embodiment. The pump beam generating unit 11 of the present embodiment includes, for example, a light source and a condensing optical system. This condensing optical system can irradiate an irradiation surface with spotted light from the light source. The pump beam generating unit 11 emits pump beam 65 toward the surface 41 of the object 40. The pump beam 65 emitted by the pump beam generating unit 11 is absorbed in the surface of the object 40 or in the vicinity of the surface in the object 40. At this time, stress is generated in accordance with a distribution of light absorption density in the object 40 and the elastic wave (an acoustic wave) is generated in the vicinity of the irradiated surface (the surface 41). A pulse width of the elastic wave (a thickness in the Z direction) has about the same value as in a light intrusion length (light penetration depth) of the pump beam 65. Here, the light intrusion length indicates a typical depth in the Z direction along which the light can intrude into the object 40.

The light source of the pump beam generating unit 11 according to the present embodiment is, for example, a YAG laser. Furthermore, the pump beam 65 to be emitted by the pump beam generating unit 11 is short pulse laser light. Here, in the present embodiment, as to the short pulse laser light for use as the pump beam 65, a pulse width (the pulse width to a time-series change of a laser strength) is, for example, a picosecond or less, for example, several 100 fs (femtoseconds). Additionally, a wavelength of the pump beam 65 is, for example, 532 nm (second harmonic).

However, the light source of the pump beam generating unit 11 and the wavelength and pulse width of the light to be emitted from the light source are not limited to those mentioned above. For example, there are not any restrictions on the light source of the pump beam 65 as long as the light source is selected in accordance with physical properties of the sample for use as the object 40, a wavelength required for the pump beam 65, or the like, and the light source may be a solid laser such as a YVO4 laser or a YLF laser, or a gas laser such as an excimer laser.

A probe beam generating unit 12 according to the present embodiment includes, for example, an X-ray light source and a condensing optical system. This condensing optical system can irradiate an irradiation surface with spotted light emitted from the X-ray light source as parallel light. The probe beam generating unit 12 emits probe beam 51 so that the light enters the surface 41 of the object 40 at an incident angle θ. Here, the incident angle θ includes, as an oblique visual angle, an angle in the vicinity of Bragg angle which satisfies Bragg conditions of a crystal structure of the object 40. Specifically, a sum of the incident angle θ and the Bragg angle has a value in the vicinity of π/2.

A photodetector 13 according to the present embodiment comprises a light receiving surface 20. The photodetector 13 is configured to detect an incident position (a light position) of the probe beam 51 emitted by the probe beam generating unit 12 and transmitted or passed through the object 40, into the light receiving surface 20. The photodetector 13 outputs the acquired light position to a processing circuit 14. The photodetector 13 may be any light receiving element as long as the element can measure a light receiving position (the light position) of an X-ray of, for example, a line sensor, an area sensor or the like.

Next, description will be made as to an operation of the optical test apparatus 10 according to the present embodiment with reference to the drawings.

For example, as shown in FIG. 7, the probe beam generating unit 12 according to the present embodiment emits X-ray light as the probe beam 51 so that the light enters the surface 41 of the object 40 at the incident angle θ in which the oblique visual angle is in the vicinity of the Bragg angle. The probe beam 51 which has intruded into the object 40 from the surface 41 is transmitted or passed through the object 40 to exit from the back surface 42. At this time, the probe beam 51 is refracted in the interface 64 to change its light direction, and then exits from the interface 64, to return to its state when the light enters the interface 64. Therefore, it can be considered that the light direction of the probe beam 51 of the present embodiment does not change even when the light passes through the interface 64. The probe beam 51 (the passed light) which exits from the back surface 42 is received by the light receiving surface 20 of the photodetector 13. At this time, the photodetector 13 detects a light position P in the light receiving surface 20 and outputs information concerning the light position P as a light receiving signal to the processing circuit 14. The processing circuit 14 acquires, from the photodetector 13, the information concerning the light position P of the probe beam 51 (the passed light) before the pump beam 65 is emitted, i.e., before the elastic wave is excited in the object 40, as information concerning a standard light position, to record the information. It is to be noted that in this recording, the value may be temporarily held.

For example, as shown in FIG. 7, the pump beam generating unit 11 according to the present embodiment irradiates the surface 41 of the object 40 with the pump beam 65. The pump beam 65 is absorbed in the vicinity of the surface 41 of the object 40. At this time, the stress is generated in the vicinity of the surface 41 in accordance with the light absorption density distribution of the object 40, and the acoustic plane wave (the elastic wave) is generated in the vicinity of the irradiated surface (the surface 41). The pulse width (the thickness in the Z direction) of the elastic wave generated in this manner is substantially equal to the light intrusion length of the pump beam 65.

Figure 8:
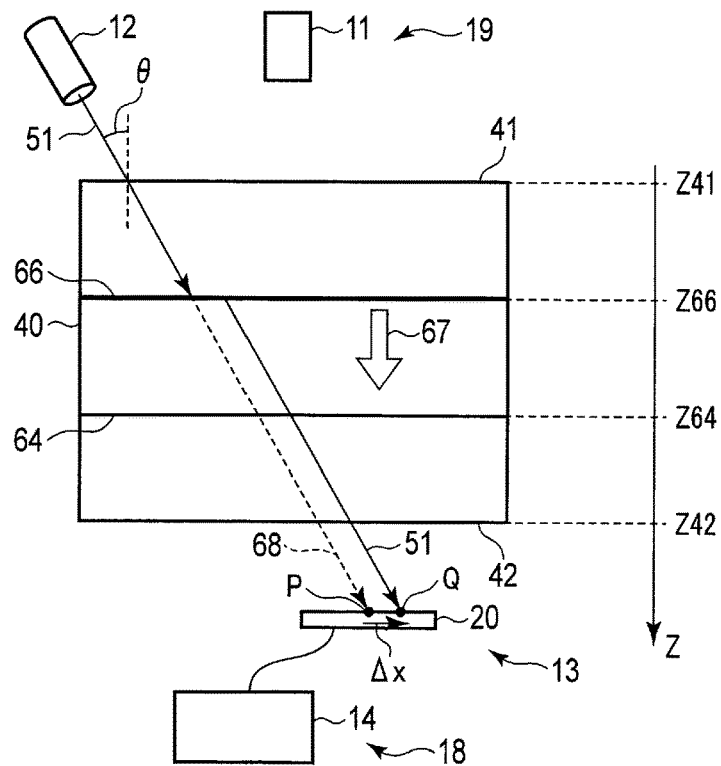
FIG. 8 is a schematic diagram to explain a measurement principle of the optical test apparatus according to the third embodiment, and shows a state before an acoustic plane wave which propagates in an object reaches an interface.

Here, FIG. 8 is a schematic diagram showing states of the optical test apparatus 10 and the object 40 before the acoustic plane wave (an elastic wave 66) which propagates in the object 40 reaches the interface 64. The elastic wave 66 generated in the vicinity of the surface 41 propagates in the Z+ direction as shown by a propagating direction 67 in the object 40. Here, a position of the elastic wave 66 in the Z direction is denoted with Z66. In other words, FIG. 8 shows the state where the elastic wave 66 propagates in the Z+ direction and where the position Z66 of the elastic wave 66 is between the position Z41 and the position Z64.

Figure 9:
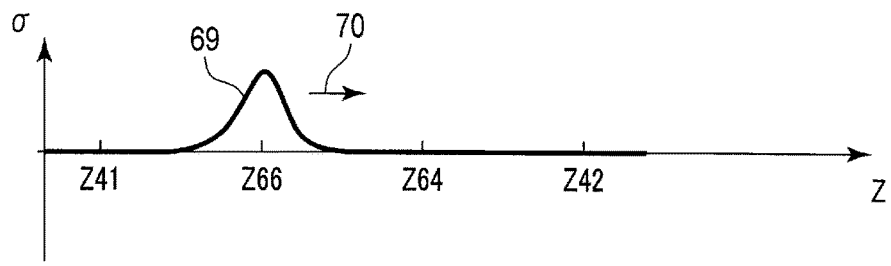
FIG. 9 is a schematic diagram to explain propagation of a strain in the object according to the third embodiment, and shows a state before the acoustic plane wave which propagates in the object reaches the interface.

In this way, the elastic wave 66 which propagates in the object 40 causes propagation of a local strain of the object 40 on the basis of the stress generated in the vicinity of the surface 41, in the object 40. Here, FIG. 9 is a schematic diagram showing one example of an internal strain distribution of the object 40 in the state shown in FIG. 8. In a graph shown in FIG. 9, the abscissa indicates positions in the object 40 in the Z direction, and the ordinate indicates a strain quantity σ in the object 40. As shown in FIG. 9, the strain is locally generated at the position Z66 at which the elastic wave 66 is present. Furthermore, this strain distribution propagates in the Z+ direction shown by a direction 70, following the propagation of the elastic wave 66 in the Z+ direction.

As shown in FIG. 8, the X-ray (the probe beam 51) which enters the object 40 at the incident angle θ in the vicinity of the oblique visual angle satisfying the Bragg conditions laterally slides dependently on the propagating direction of the strain by the elastic wave 66. That is, the light path (the light position) of the probe beam 51 (the passed light) which has passed the elastic wave 66 is changed by the elastic wave 66. For example, as shown in FIG. 8, the light path of the passed light (the probe beam 51) after the light position is changed is not present on an extension line of the light path which is shown by a broken line 68 before the light reaches the elastic wave 66, and the light path is parallel to the broken line 68. It is to be noted that the above-mentioned direction of the strain is not the direction 70 in which the strain propagates, but indicates whether the strain quantity σ is positive or negative.

The probe beam 51 laterally slid by the elastic wave 66 exits from the back surface 42 and enters the light receiving surface 20. The photodetector 13 detects a light position Q (the light receiving position) in the light receiving surface 20 of the probe beam 51 (the passed light) laterally slid by the elastic wave 66, and the unit outputs information concerning the light position Q (information concerning a passing light position) as the light receiving signal to the processing circuit 14.

The processing circuit 14 acquires the information concerning the light position Q of the probe beam 51 laterally slid by the elastic wave excited in the object 40 irradiated with the pump beam 65 as the information concerning the passing light position, to record the information. It is to be noted that in this recording, the value may be temporarily held. Then, the processing circuit 14 compares the light position Q (the information concerning the passing light position) with the light position P (the information concerning the standard light position), and calculates a lateral slide quantity Δx from a shift quantity of the light position in the light receiving surface 20 of an X-ray receiving element.

Figure 10:
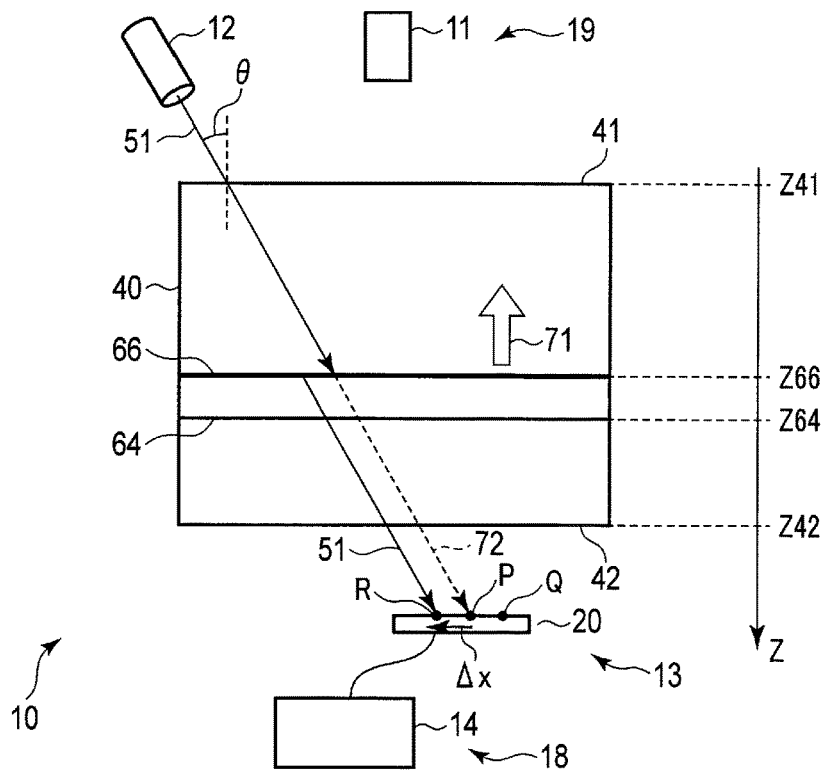
FIG. 10 is a schematic diagram to explain a measurement principle of the optical test apparatus according to the third embodiment, and shows a state after an acoustic plane wave which propagates in the object reaches the interface and is reflected.

Here, FIG. 10 is a schematic diagram showing states of the optical test apparatus 10 and the object 40 after the acoustic plane wave (the elastic wave 66) which propagates in the object 40 reaches the interface 64. The elastic wave 66 which reaches the interface 64 is reflected by the interface 64 due to a difference of a refractive index of the object 40 which is made via the interface 64. The elastic wave 66 reflected by the interface 64 propagates in the Z− direction shown by a propagating direction 71. In other words, FIG. 10 shows a state where the elastic wave 66 propagates in the Z− direction and where the position Z66 of the elastic wave 66 is present between the position Z41 and the position Z64.

Figure 11:
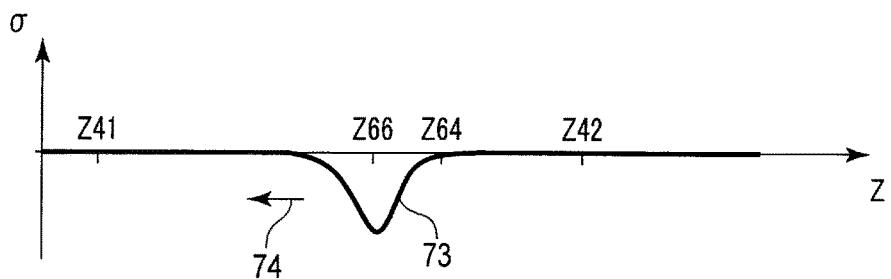
FIG. 11 is a schematic diagram to explain the propagation of the strain in the object according to the third embodiment, and shows a state after the acoustic plane wave which propagates in the object reaches the interface and is reflected.

Here, FIG. 11 is a schematic diagram showing one example of an internal strain distribution of the object 40 in the state shown in FIG. 10. In a graph shown in FIG. 11, the abscissa indicates the positions in the object 40 in the Z direction, and the ordinate indicates the strain quantity σ in the object 40. As shown in FIG. 11, the strain is locally generated at the position Z66 at which the elastic wave 66 is present. Furthermore, this strain distribution propagates in the Z− direction shown by a direction 74, following the propagation of the elastic wave 66 in the Z− direction.

In the direction of the strain propagated by the elastic wave 66 (positive/negative of the strain quantity σ), the sign is inverted due to a difference in density of the object 40 which is made via the interface 64, when the elastic wave 66 is reflected by the interface 64. For example, the elastic wave 66 which propagates the positive strain quantity σ from the surface 41 in the Z+ direction is reflected by the interface 64 as shown in FIG. 9, and then, the elastic wave 66 propagates the negative strain quantity σ from the interface 64 in the Z− direction as shown in FIG. 11.

Thus, in the state shown in FIG. 10, the direction of the strain propagated by the elastic wave 66 is inverted from the state shown in FIG. 8. As described above, the X-ray (the probe beam 51) which enters the object 40 at the incident angle θ in which the oblique visual angle is in the vicinity of the Bragg angle laterally slides dependently on the direction of the strain propagated by the elastic wave 66. Specifically, the light path of the probe beam 51 (the passed light) which has passed the elastic wave 66 as shown in FIG. 10 is inverted from the light path of the probe beam 51 which has passed the elastic wave 66 as shown in FIG. 8, and the light path is present at an inverted position to an extension line of the light path which is shown by a broken line 72 before the light reaches the elastic wave 66.

The photodetector 13 detects a light position R of the probe beam 51 (the passed light) laterally slid by the elastic wave 66 to change its light position as shown in FIG. 10, in the light receiving surface 20, and the unit outputs information concerning the light position R as a light receiving signal to the processing circuit 14.

The processing circuit 14 acquires, from the photodetector 13, the light position R of the probe beam 51 (the passed light) laterally slid by the elastic wave which propagates from the interface 64 toward the surface 41 after the elastic wave 66 is reflected by the interface 64, to record the position as the information concerning the passing light position. It is to be noted that in this recording, the value may be temporarily held. Then, the processing circuit 14 compares the light position R (the information concerning the passing light position) with the light position P (the information concerning the standard light position), and calculates a lateral slide quantity from a shift quantity of the light position in the light receiving surface 20 of the X-ray receiving element. It is to be noted that the lateral slide quantity calculated herein is denoted with, for example, −Δx.

In this way, when the elastic wave 66 reaches the interface and is reflected, the sign of the lateral slide quantity detected by the photodetector 13 changes, and hence, the light receiving signal to be output by the photodetector 13 changes. Specifically, the optical test apparatus 10 of the present embodiment can measure a time-series change of the light receiving signal, and calculates a time (a propagation time) from when the elastic wave 66 is excited in the surface 41 and propagates in the object 40 until the wave reaches the interface 64 or from when the elastic wave 66 is reflected by the interface 64 and propagates in the object 40 until the wave reaches the surface 41.

The elastic wave 66 travels at a sound speed peculiar to the object 40, in the object 40. For example, the sound speed of amorphous carbon is about 6 nm/ps. Specifically, when the speed of the elastic wave 66 is known in this manner, the optical test apparatus 10 of the present embodiment has an effect that a thickness of a film between the surface 41 and the interface 64 in the object 40 can be measured on the basis of the propagation time of the elastic wave 66 which is calculated as described above, and the sound speed.

Additionally, in the present embodiment, the description has been made as to the example where the object 40 has the interface 64, but the present embodiment is not limited to this example. The elastic wave 66 can be reflected, for example, by the back surface 42 of the object 40 which does not have the interface 64 therein. In this case, the refractive index of the object 40 is different from a refractive index outside the object 40 via the back surface 42 of the object 40. In other words, the back surface 42 can be the interface 64 which is present in the object 40. Therefore, by use of the optical test apparatus 10 of the present embodiment, a thickness of the object 40 of a single layer can be measured.

The optical test apparatus 10 according to the present embodiment can be concluded as follows.

The optical test apparatus 10 according to the present embodiment comprises the photodetector 13 which outputs the information concerning the light position of the received light as the light receiving signal, and the processing circuit 14 which processes the light receiving signal to acquire the information concerning the standard light position (the light position P) as a standard and the information concerning the passing light position (the light position Q or the light position R) of the light which has passed through the object 40, compares the information concerning the passing light position with the information concerning the standard light position, and on the basis of results of the comparison (the lateral slide quantity), acquires information concerning internal physical quantities of the object. According to this constitution, presence/absence of the strain of the acoustic plane wave (e.g., the elastic wave 66) or the like in the object 40 can be detected and acquired without contact.

The optical test apparatus 10 according to the present embodiment further comprises the probe beam generating unit 12 which emits, as the light, the probe beam 51 having a wavelength transmittable (or passable) through the object 40 to the standard light position, and the acoustic wave generating unit 19 (the pump beam generating unit 11) which generates the acoustic wave (the elastic wave 66) reflected by the interface 64 present in the object 40 to change its propagating direction, so that the passing light position can change in accordance with the change of the propagating direction. The processing circuit 14 acquires a thickness of the object 40 between the surface 41 of the object on the side on which the acoustic wave generating unit 19 (the pump beam generating unit 11) is positioned and the interface 64 as the information concerning the internal physical quantities of the object 40 on the basis of the propagation speed of the acoustic wave (the elastic wave 66) and the time-series change of the passing light position to the standard light position.

According to this constitution, the lateral slide of the probe beam 51 (the passed light) is caused in accordance with the direction of the strain of the elastic wave 66 and the passing light position can be changed to the standard light position. That is, the passing light position to the standard light position can be changed in accordance with the propagating direction of the elastic wave 66. Therefore, the propagation time of the elastic wave 66 between the surface 41 and the interface 64 can be acquired as the time from when the elastic wave 66 is generated until the sign of the lateral slide quantity calculated by comparison of the passing light position with the standard light position changes. It is to be noted that the propagation time of the elastic wave 66 between the surface 41 and the interface 64 can be calculated as the time from when the elastic wave 66 is reflected by the interface 64 until the sign of the lateral slide quantity calculated by the comparison of the passing light position with the standard light position changes. Here, when the propagation speed of the elastic wave 66 is known, the thickness (film thickness) between the surface 41 and the interface 64 can be acquired. It is to be noted that the back surface 42 can be included in the interface 64 which is present in the object 40. Therefore, when the object 40 is a single layer, the thickness of the object 40 can be acquired.

In the optical test apparatus 10 according to the present embodiment, the time-series change of the passing light position to the standard light position includes information concerning a time from when the passing light position to the standard light position changes until the light position further changes. Here, the propagation time of the elastic wave 66 may be calculated as an average value from a time for which the passing light position changes a plurality of times, for example, a time from when the elastic wave 66 starts to propagate from the surface 41, is reflected by the interface 64 and then reaches the surface 41 again, and the number of the times of the change.

The probe beam generating unit 12 of the optical test apparatus 10 according to the present embodiment is configured to emit the X-ray as the probe beam 51 so that the probe beam 51 enters the object 40 at the incident angle θ in the vicinity of the angle which satisfies the Bragg conditions. According to this constitution, the probe beam 51 can enter the object 40, and hence, the lateral slide of the probe beam 51 in accordance with the direction of the strain of the elastic wave 66 can be caused. Therefore, the information concerning the internal physical quantities of the object 40 can be acquired on the basis of the change of the light position. Furthermore, by use of the X-ray having a high straightness as the probe beam 51, there is the effect that the wave front of the elastic wave 66 does not have to be orthogonal to a straight line which passes the probe beam generating unit 12 and the photodetector 13.

The acoustic wave generating unit 19 (the pump beam generating unit 11) of the optical test apparatus 10 according to the present embodiment emits the short pulse laser light toward the object 40, to generate the acoustic wave (the elastic wave 66). According to this constitution, when the object 40 is, for example, the solid, the steep elastic wave 66 can be generated in the vicinity of the surface 41 of the object 40, and hence, improvement of a detection accuracy is achievable.

The acoustic wave generating unit 19 (the pump beam generating unit 11) of the optical test apparatus 10 according to the present embodiment propagates the acoustic wave (the elastic wave 66) along the straight line connecting the probe beam generating unit 12 to the photodetector 13. According to this constitution, the passing light position of the probe beam 51 (the passed light) can be changed in accordance with the strain direction of the elastic wave 66.

An optical test method according to the present embodiment includes receiving the passed light (the probe beam 51) which has passed through the object 40, acquiring the information concerning the standard light direction that is the standard as standard light information, acquiring the information concerning the passing light position of the received passed light (the probe beam 51) as passing light information, comparing the standard light information with the passing light information, and on the basis of results of the comparison, acquiring the information concerning the internal physical quantities of the object 40. Here, the standard light information is the standard light position, an output value of the photodetector 13 which can be converted to the standard light position, or the like. Furthermore, the passing light information is the passing light position, an output value of the photodetector 13 which can be converted to the passing light direction, or the like. Additionally, the results of the comparison is a displacement quantity from the standard light position to the passing light position, a sign of the displacement quantity, a time-series change of the passing light position to the standard light position, or the like. According to this method, the above-mentioned effects are obtainable.

It is to be noted that the above respective embodiments and the respective modifications can suitably be combined to achieve one embodiment. For example, it is possible to combine the modification concerning the acquisition of the light direction in the first embodiment or the modification of the first embodiment with the second embodiment or to combine, for example, the first embodiment with the first modification of the second embodiment.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. An optical test apparatus comprising:
a probe beam generating unit which emits a probe beam in a standard light direction,
an acoustic wave generating unit configured to generate an acoustic plane wave which propagates in the standard light direction, the acoustic plane wave generating a diffracted wave which propagates in a direction different from the standard light direction by interference of a refractive index distribution on a propagation path of the acoustic plane wave, the diffracted wave deflecting the probe beam by changing a refractive index distribution on a light path of the probe beam,
a photodetector which receives the probe beam which has passed through an object and outputs a light receiving signal corresponding to a light direction of the received probe beam, and
a processing circuit which processes the light receiving signal to acquire a time-series change of the light direction of the received probe beam to the standard light direction, and on the basis of the time-series change, acquires presence/absence or change of the refractive index distribution on the propagation path of the acoustic plane wave in the object.

2. The optical test apparatus according to claim 1, wherein the processing circuit acquires a light direction of the probe beam in a standard state as the standard light direction.

3. The optical test apparatus according to claim 1, wherein the photodetector comprises a light receiving optical system which adjusts a light position of the probe beam to the light position corresponding to the light direction, and a light receiving surface configured to detect the light position,
and
the processing circuit acquires the light direction of the probe beam based on the detected light position.

4. The optical test apparatus according to claim 1, wherein the photodetector outputs a light receiving signal corresponding to the light direction of the received probe beam with respect to each of at least two wavelengths, and
the processing circuit acquires a wavelength dependency of a refractive index distribution on a light path of the probe beam, on the basis of the time-series change concerning the at least two wavelengths, and further acquires information concerning a substance constituting the object, on the basis of the wavelength dependency.

5. The optical test apparatus according to claim 1, wherein a wave front of the acoustic plane wave is substantially orthogonal to a straight line connecting the probe beam generating unit to the photodetector.

6. The optical test apparatus according to claim 1, wherein the acoustic wave generating unit emits short pulse laser light toward the object, to generate the acoustic plane wave.

7. An optical test apparatus comprising:
a probe beam generating unit which emits probe beam having a wavelength transmittable through an object to a standard light position,
an acoustic wave generating unit which generates an acoustic wave reflected by an interface which is present in the object to change its propagating direction, and configured to change a light position of the received probe beam in accordance with the change of the propagating direction,
a photodetector which receives the probe beam which has passed through the object and outputs a light receiving signal corresponding to a light position of the received probe beam, and
a processing circuit which processes the light receiving signal to acquire a time-series change of the light position of the probe beam which has passed through the object to the standard light position, and on the basis of a propagation speed of the acoustic wave and the time-series change, acquires a thickness between the interface and a surface of the object on a side on which the acoustic wave generating unit is positioned.

8. The optical test apparatus according to claim 7, wherein the time-series change includes information concerning a time from when the light position of the probe beam to the standard light position changes until the light position further changes.

9. The optical test apparatus according to claim 7, wherein the probe beam generating unit is configured to emit an X-ray as the probe beam so that the probe beam enters the object at an incident angle in the vicinity of an angle which satisfies Bragg conditions.

10. The optical test apparatus according to claim 7, wherein the acoustic wave generating unit emits short pulse laser light toward the object, to generate the acoustic wave.

11. The optical test apparatus according to claim 7, wherein the acoustic wave generating unit propagates the acoustic wave along a straight line connecting the probe beam generating unit to the photodetector.

12. An optical test method comprising:

emitting probe beam in a standard light direction, generating an acoustic plane wave which propagates in the standard light direction, the acoustic plane wave generating a diffracted wave which propagates in a direction different from the standard light direction by interference of a refractive index distribution on a propagation path of the acoustic plane wave, the diffracted wave deflecting the probe beam by changing a refractive index distribution on a light path of the probe beam, receiving the probe beam which has passed through an object, processing the light receiving signal corresponding to a light direction of the received probe beam to acquire a time-series change of the light direction of the probe beam to the standard direction, and on the basis of the time-series change, acquiring presence/absence or change of the refractive index distribution on the propagation path of the acoustic plane wave in the object.

* * * * *